United States Patent
Levins et al.

(10) Patent No.: US 9,758,618 B2
(45) Date of Patent: *Sep. 12, 2017

(54) ULTRAVIOLET RADIATION ABSORBING POLYETHERS

(71) Applicant: JOHNSON & JOHNSON CONSUMER INC., Skillman, NJ (US)

(72) Inventors: Christopher G. Levins, Flemington, NJ (US); Joseph F. Zavatsky, Flemington, NJ (US); Aruna Nathan, Bridgewater, NJ (US); Susan Daly, Basking Ridge, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,591

(22) Filed: Jan. 27, 2016

(65) Prior Publication Data

US 2016/0137780 A1    May 19, 2016

Related U.S. Application Data

(63) Continuation of application No. 13/799,222, filed on Mar. 13, 2013, now Pat. No. 9,255,180.

(60) Provisional application No. 61/665,439, filed on Jun. 28, 2012.

(51) Int. Cl.
  *C08G 65/333*   (2006.01)
  *A61K 8/86*     (2006.01)
  *A61Q 17/04*    (2006.01)
  *C08G 65/332*   (2006.01)

(52) U.S. Cl.
  CPC .......... *C08G 65/33396* (2013.01); *A61K 8/86* (2013.01); *A61Q 17/04* (2013.01); *C08G 65/333* (2013.01); *C08G 65/3326* (2013.01); *A61K 2800/57* (2013.01)

(58) Field of Classification Search
  None
  See application file for complete search history.

(56) References Cited

U.S. PATENT DOCUMENTS

| | | |
|---|---|---|
| 4,107,290 A | 8/1978 | Jacquet et al. |
| 4,322,522 A | 3/1982 | Johnson et al. |
| 4,399,297 A | 8/1983 | Thoemel et al. |
| 4,528,311 A | 7/1985 | Beard et al. |
| 4,839,160 A | 6/1989 | Forestier et al. |
| 4,897,259 A | 1/1990 | Murray et al. |
| 5,039,782 A | 8/1991 | Langer et al. |
| 5,138,089 A | 8/1992 | Sabatelli |
| 5,157,091 A | 10/1992 | Masataka et al. |
| 5,166,234 A | 11/1992 | Kawaguchi et al. |
| 5,250,652 A | 10/1993 | Langer et al. |
| 5,399,371 A | 3/1995 | Harris |
| 5,459,222 A | 10/1995 | Rodgers et al. |
| 5,487,885 A | 1/1996 | Sovak et al. |
| 5,585,090 A | 12/1996 | Yoshioka et al. |
| 5,741,924 A | 4/1998 | Sovak et al. |
| 5,843,410 A | 12/1998 | Kim et al. |
| 5,869,030 A | 2/1999 | Dumler et al. |
| 5,869,099 A | 2/1999 | Keller et al. |
| 6,001,337 A | 12/1999 | Keller et al. |
| 6,048,516 A | 4/2000 | Bringhen et al. |
| 6,123,928 A | 9/2000 | Sovak et al. |
| 6,143,850 A | 11/2000 | Keller et al. |
| 6,183,728 B1 | 2/2001 | Forestier et al. |
| 6,193,959 B1 | 2/2001 | Bernasconi et al. |
| 6,294,156 B1 | 9/2001 | Lentini et al. |
| 6,391,287 B1 | 5/2002 | Baldo et al. |
| 6,413,393 B1 | 7/2002 | Van Antwerp et al. |
| 6,471,949 B2 | 10/2002 | Candau et al. |
| 6,540,986 B2 | 4/2003 | Lukenbach et al. |
| 6,620,407 B1 | 9/2003 | Gers-Barlag et al. |
| 6,620,904 B2 | 9/2003 | Lemke |
| 6,767,547 B2 | 7/2004 | Gers-Barlag et al. |
| 6,800,274 B2 | 10/2004 | Bonda et al. |
| 6,814,959 B1 | 11/2004 | Muller et al. |
| 6,867,250 B1 | 3/2005 | Gupta et al. |
| 6,869,597 B2 | 3/2005 | Arnaud |
| 6,881,415 B1 | 4/2005 | Gers-Barlag et al. |
| 6,899,866 B2 | 5/2005 | Bonda |
| 6,905,674 B2 | 6/2005 | L'Alloret |
| 6,951,911 B2 | 10/2005 | Tagawa et al. |
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |

(Continued)

FOREIGN PATENT DOCUMENTS

| | | |
|---|---|---|
| EP | 407932 A | 1/1991 |
| EP | 413648 A | 2/1991 |
| EP | 523955 A | 1/1993 |
| EP | 601080 B | 7/1995 |
| EP | 681830 A | 11/1995 |

(Continued)

OTHER PUBLICATIONS

U.S. Appl. No. 61/665,464, filed Jun. 28, 2012, Daly et al.
U.S. Appl. No. 61/665,430, filed Jun. 28, 2012, Levins et al.
U.S. Appl. No. 61/665,439, filed Jun. 28, 2012, Levins et al.
U.S. Appl. No. 61/991,732, filed May 12, 2014, Daly et al.
"Crodacol™ C95 Product Details" from the Croda website, 2013 http://www.croda.com/home.aspx?view=dtl&d=content&s=157&r=401&p=2578&prodID-1779.
Erberich et al., "Polyglycidols with Two Orthogonal Protective Groups: Preparation, Selective Deprotection, and Functionalization", *Macromolecules* (2007), vol. 40, pp. 3070-3079.

(Continued)

*Primary Examiner* — Brian Gulledge

(57) ABSTRACT

A polymer composition comprising a linear ultraviolet radiation absorbing polyether that comprises a chemically bound UV-chromophore.

13 Claims, No Drawings

(56) References Cited

U.S. PATENT DOCUMENTS

| | | |
|---|---|---|
| 7,465,438 B2 | 12/2008 | Schunicht et al. |
| 7,534,420 B2 | 5/2009 | Bonda et al. |
| 7,749,524 B2 | 7/2010 | Lu et al. |
| 7,850,954 B2 | 12/2010 | Leblanc et al. |
| 7,914,775 B2 | 3/2011 | Cottard et al. |
| 7,988,953 B2 | 8/2011 | Poschalko et al. |
| 7,993,680 B2 | 8/2011 | Clemente et al. |
| 8,003,132 B2 | 8/2011 | Clemente et al. |
| 8,025,868 B2 | 9/2011 | Clemente et al. |
| 8,211,850 B2 | 7/2012 | Andjelic et al. |
| 8,394,755 B2 | 3/2013 | Andjelic et al. |
| 9,248,092 B2* | 2/2016 | Daly .................. A61K 8/55 |
| 9,254,254 B2* | 2/2016 | Daly .................. A61K 8/55 |
| 9,255,180 B2* | 2/2016 | Levins ................ A61K 8/86 |
| 2001/0038829 A1 | 11/2001 | Hasebe et al. |
| 2002/0131941 A1 | 9/2002 | Habeck et al. |
| 2002/0155073 A1 | 10/2002 | Fankhauser et al. |
| 2003/0165553 A1 | 9/2003 | Gers-Barlag et al. |
| 2004/0019220 A1 | 1/2004 | Fischer et al. |
| 2004/0022836 A1 | 2/2004 | Degen et al. |
| 2004/0057914 A1 | 3/2004 | Bonda et al. |
| 2004/0096406 A1 | 5/2004 | De Poilly |
| 2004/0126339 A1 | 7/2004 | Roszell |
| 2004/0197359 A1 | 10/2004 | Yamada et al. |
| 2004/0223925 A1 | 11/2004 | L'Alloret |
| 2004/0228814 A1 | 11/2004 | Candau et al. |
| 2005/0031660 A1 | 2/2005 | Deckner |
| 2005/0036961 A1 | 2/2005 | Hansenne et al. |
| 2005/0048010 A1 | 3/2005 | Kliss et al. |
| 2005/0065251 A1 | 3/2005 | Candau et al. |
| 2005/0180933 A1 | 8/2005 | Wei et al. |
| 2006/0204457 A1 | 9/2006 | Toda et al. |
| 2007/0098653 A1 | 5/2007 | Tamasawa et al. |
| 2007/0134174 A1 | 6/2007 | Irwin et al. |
| 2008/0081025 A1* | 4/2008 | Poschalko ............. A61K 8/445 424/60 |
| 2008/0089852 A1 | 4/2008 | Hotz et al. |
| 2008/0247975 A1 | 10/2008 | Dueva-Koganov et al. |
| 2008/0311234 A1 | 12/2008 | Yoneda et al. |
| 2009/0016971 A1 | 1/2009 | Gaudry et al. |
| 2009/0041688 A1 | 2/2009 | Dueva-Koganov et al. |
| 2009/0068130 A1 | 3/2009 | Spaulding et al. |
| 2009/0185988 A1 | 7/2009 | Maleski et al. |
| 2009/0214460 A9 | 8/2009 | Luukas |
| 2009/0232859 A1 | 9/2009 | Sakuta et al. |
| 2009/0258230 A1 | 10/2009 | Schlossman et al. |
| 2009/0297462 A1 | 12/2009 | Hessefort et al. |
| 2009/0324523 A1 | 12/2009 | Clemente et al. |
| 2009/0324524 A1 | 12/2009 | Clemente et al. |
| 2010/0003202 A1 | 1/2010 | Matsumoto et al. |
| 2010/0129303 A1 | 5/2010 | Dueva-Koganov et al. |
| 2010/0189661 A1 | 7/2010 | Musa et al. |
| 2010/0226867 A1 | 9/2010 | Dueva-Koganov et al. |
| 2010/0239508 A1 | 9/2010 | Mori et al. |
| 2010/0284948 A1 | 11/2010 | Ohrmann et al. |
| 2011/0014139 A1 | 1/2011 | Viala et al. |
| 2011/0027202 A1 | 2/2011 | Candau et al. |
| 2011/0104078 A1 | 5/2011 | Burgo et al. |
| 2011/0117034 A1* | 5/2011 | Satonaka ............. A61K 8/39 424/59 |
| 2011/0195036 A1 | 8/2011 | Clemente et al. |
| 2012/0058974 A1 | 3/2012 | Misske et al. |
| 2012/0087882 A1 | 4/2012 | Fevola et al. |
| 2012/0093753 A1 | 4/2012 | Fevola et al. |
| 2012/0294813 A1 | 11/2012 | Frey et al. |
| 2013/0115179 A1 | 5/2013 | Janssen et al. |
| 2014/0004054 A1 | 1/2014 | Daly et al. |
| 2014/0004055 A1 | 1/2014 | Daly et al. |
| 2014/0004056 A1 | 1/2014 | Daly et al. |
| 2014/0004057 A1 | 1/2014 | Daly et al. |
| 2014/0004058 A1 | 1/2014 | Daly et al. |
| 2014/0004059 A1 | 1/2014 | Daly et al. |
| 2014/0004060 A1 | 1/2014 | Levins et al. |
| 2014/0004061 A1 | 1/2014 | Levins et al. |
| 2014/0004063 A1 | 1/2014 | Daly |
| 2014/0004064 A1 | 1/2014 | Daly |
| 2015/0164771 A1 | 6/2015 | Daly et al. |
| 2015/0320671 A1 | 11/2015 | Daly et al. |

FOREIGN PATENT DOCUMENTS

| | | |
|---|---|---|
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| EP | 2679616 A | 1/2014 |
| JP | S6099186 A | 6/1985 |
| JP | 2006-265389 A | 10/2006 |
| JP | 2009-167168 A | 7/2009 |
| WO | WO 92/19592 A | 11/1992 |
| WO | WO 93/22366 A | 11/1993 |
| WO | WO 93/22413 A | 11/1993 |
| WO | WO 96/03369 A | 2/1996 |
| WO | WO 01/08647 A | 2/2001 |
| WO | WO 02/24668 A | 3/2002 |
| WO | WO 02/36534 A | 5/2002 |
| WO | WO 2004/009047 A | 1/2004 |
| WO | WO 2005/092282 A | 10/2005 |
| WO | WO 2007/066309 A | 6/2007 |
| WO | WO 2007/081209 A | 7/2007 |
| WO | WO 2008/056678 A | 5/2008 |
| WO | WO 2010/060776 A | 6/2010 |
| WO | WO 2010/115009 A | 10/2010 |
| WO | WO 2011/048570 A | 4/2011 |
| WO | WO 2011/070050 A | 6/2011 |
| WO | WO 2011/070053 A | 6/2011 |
| WO | WO 2011/070073 A | 6/2011 |
| WO | WO 2011/070075 A | 6/2011 |
| WO | WO 2011/070077 A | 6/2011 |
| WO | WO 2014/004474 A | 1/2014 |
| WO | WO 2014/004477 A | 1/2014 |

OTHER PUBLICATIONS

Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.

Fitton et al., Synthesis (1987), pp. 1140-1142.

Hanson et al., "Sunscreen Enhancement of UV-induced Reactive Oxygen Species in the Skin", *Free Radical Biology & Medicine* (2006) vol. 41, pp. 1205-1212.

Haouet et al., "Preparation Et Proprietes Des Poly®—Glycidols", *European Polymer Journal* (1983), vol. 19(12), pp. 1089-1098. (English Abstract).

Kuhn et al., "Monitoring the Kinetics of Ion-Dependent Protein Folding by Time-Resolved NMR Spectroscopy at Atomic Resolution", *Journal of the American Chemical Society* (2000), vol. 122, pp. 6169-6174.

Lee et al., "Poly(allyl Glycidyl Ether)—A Versatile and Functional Polyether Platform", *Journal of Polymer Science Part A: Polymer Chemistry* (2011), vol. 49, pp. 4498-4504.

Li et al., "Synthesis of polyethylene glycol (PEG) derivatives and PEGylated-peptide biopolymer conjugates", *Biomacromolecules*, American Chemical Society, US, vol. 4, No. 4, May 17, 2003, pp. 1055-1067 (ISSN: 1525-7797, DOI: 10.1021/BM034069L) (XP002328259).

Moore et al., "Room Temperature Polyesterification", *Macromolecules* (1990), vol. 23, Issue 1, pp. 65-70.

Obermeier et al., "Poly(ethylene glycol-co-allyl glycidyl ether)s: A PEG-Based Modular Synthetic Platform for Multiple Bioconjugation", Bioconjugate Chemistry (2011), vol. 22, pp. 436-444.

Rokicki et al., "Hyperbranched aliphatic polyethers obtained from environmentally benign monomer: glycerol carbonate", *Green Chemistry* (2005), vol. 7, pp. 529-539.

Stiriba et al., "Hyperbranched molecular nanocapsules: Comparison of the hyperbranched architecture with the perfect linear analogue", Journal of the American Chemical Society (2002) vol. 124, pp. 9698-9699.

(56) References Cited

OTHER PUBLICATIONS

Sunder et al., "Controlled Synthesis of Hyperbranched Polyglycerols by Ring-Opening Multibranching Polymerization", *Macromolecules* (1999), vol. 32, pp. 4240-4246.

Taton et al., "Synthesis of chiral and racemic functional polymers from glycidol and thioglycidol", *Macromolecular Chemistry and Physics* (1994), vol. 195, pp. 139-148.

Tchao, "Trans-Epithelial Permeability of Fluorescein in Vitro as an Assay to Determine Eye Irritants", *Alternative Methods in Toxicology 6, Progress in In Vitro Toxicology* (ed. A.M. Goldberg) (1988), pp. 271-283.

Tokar et al., "Cationic Polymerization of Glycidol: Coexistence of the Activated Monomer and Active Chain End Mechanism", *Macromolecules* (1994), vol. 27, pp. 320-322.

\* cited by examiner

ULTRAVIOLET RADIATION ABSORBING POLYETHERS

This application is a continuation of U.S. application Ser. No. 13/799222 filed on Mar. 13, 2013, which claims the benefit of U.S. provisional application 61/665439 filed Jun. 28, 2012, the complete disclosure of which is hereby incorporated herein by reference for all purposes.

FIELD OF THE INVENTION

The invention relates to polymers bearing a UV-chromophore. More specifically, the invention relates to polymer compositions including a linear ultraviolet radiation absorbing polyether that includes a chemically bound UV-chromophore.

BACKGROUND OF THE INVENTION

Skin cancer is a significant public health concern which represents 50% of diagnosed cases of cancer in the United States. Ultraviolet radiation (UV) can cause molecular and cellular level damage, and is considered the leading environmental factor responsible for skin cancer. The prolonged exposure to UV radiation, such as from the sun, can lead to the formation of light dermatoses and erythemas, as well as increase the risk of skin cancers, such as melanoma, and accelerate skin aging processes, such as loss of skin elasticity and wrinkling.

The damaging effects of UV exposure can be suppressed by topical application of sunscreens which contain compounds that absorb, reflect or scatter UV, typically in the UVA (wavelengths from about 320 to 400 nm) or UVB (wavelengths from around 290 to 320 nm) range of the spectrum. Numerous sunscreen compounds are commercially available with varying ability to shield the body from ultraviolet light.

It has been suggested to use sunscreen molecules having high molecular weights in order to reduce the penetration of the sunscreen molecule through the epidermis. However, the inventors have recognized that it would be desirable to have entirely new polymeric sunscreen compounds (ultraviolet radiation-absorbing polymers) in order to provide any of various benefits such as improved protection from UV.

SUMMARY OF THE INVENTION

The invention includes polymer compositions including a linear ultraviolet radiation absorbing polyether that includes a chemically bound UV-chromophore, and compositions that provide protection from ultraviolet radiation and that include such UV-absorbing polymer compositions.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever. Unless defined otherwise, all technical and scientific terms used herein have the same meaning as commonly understood by one of ordinary skill in the art to which the invention belongs. With the exception of express references to number average molecular weight ($M_n$), all other references to molecular weight are weight average molecular weight ($M_w$). Also, all publications, patent applications, patents, and other references mentioned herein are incorporated by reference.

UV Absorbing Polymer

Embodiments of the invention relate to polymer compositions including an ultraviolet radiation absorbing polyether, (i.e., "UV absorbing polyether"). By UV absorbing polyether, it is meant a polyether that absorbs radiation in some portion of the ultraviolet spectrum (wavelengths between 290 and 400 nm). The UV absorbing polyether has a weight average molecular weight ($M_w$), which may be suitable for reducing or preventing the chromophore from absorbing through the skin. According to one embodiment, a suitable molecular weight for the UV absorbing polyether is $M_w$ greater than 500. In one embodiment, $M_w$ is in the range of about 500 to about 50,000. In another embodiment, the $M_w$ is in the range of about 1000 to about 20,000, such as from about 1000 to about 10,000.

Described herein is a polymer composition including a UV absorbing polyether. As one skilled in the art will recognize "polyether" indicates that the UV absorbing polymer includes a plurality of ether functional groups covalently bonded to each other. The "backbone" of the UV absorbing polyether refers to the longest continuous sequence of covalently bonded ether functional groups. Other smaller groups of covalently bonded atoms are considered pendant groups that branch from the backbone.

According to certain embodiments the polyether includes glyceryl repeat units and accordingly, may be characterized as a polyglycerol. By "glyceryl repeat units" (also referred to herein "glyceryl remnant units") it is meant glycerol units excluding nucleophilic groups such as hydroxyl groups. Glyceryl remnant units include ether functional groups, and generally may be represented as $C_3H_5O$ for linear and dendritic remnants (Rokicki et al. *Green Chemistry*, 2005, 7, 52). Suitable glyceryl remnant units include dehydrated forms (i.e. one mole of water removed) of the following glyceryl units: linear-1,4 ($L_{1,4}$) glyceryl units; linear-1,3 ($L_{1,3}$) glyceryl repeat units; dendritic (D) glyceryl units; terminal-1,2 ($T_{1,2}$) units; and terminal-1,3 ($T_{1,3}$) units. Examples of linear glyceryl remnant units and terminal units are shown below (to the right side of the arrows). The corresponding glyceryl unit before dehydration (shown to the left side of arrows; includes hydroxyls) are shown as well:

linear-1,4 ($L_{1,4}$) glyceryl repeat units

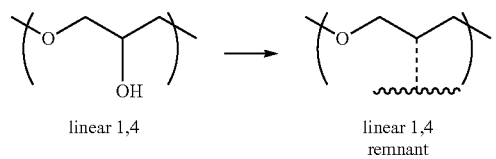

linear 1,4      linear 1,4 remnant linear-1,3 ($L_{1,3}$) glyceryl repeat units

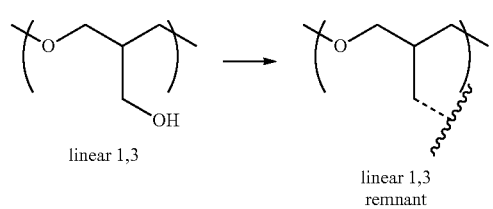

linear 1,3      linear 1,3 remnant terminal-1,2 ($T_{1,2}$) units

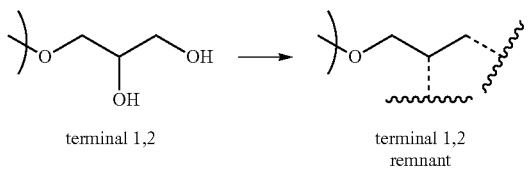

terminal 1,2         terminal 1,2 remnant and terminal-1,3 ($T_{1,3}$) units

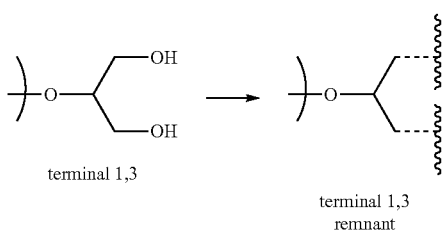

terminal 1,3         terminal 1,3 remnant

The polymer composition includes a linear ultraviolet radiation absorbing polyether that comprises a chemically bound ultraviolet radiation-absorbing chromophore ("UV-chromophore"). By linear, it is meant the UV absorbing polyether has a backbone that is unbranched.

According to certain embodiments, the polymer composition comprises about 50% or more of the linear ultraviolet radiation absorbing polyether that comprises a chemically bound UV-chromophore. According to certain other embodiments, the polymer composition comprises about 75% or more of the linear ultraviolet radiation absorbing polyether that comprises a chemically bound UV-chromophore. According to certain other embodiments, the polymer composition comprises about 90% or more of the linear ultraviolet radiation absorbing polyether, such as about 95% or more. According to certain other embodiments, in addition to the linear ultraviolet radiation absorbing polyether, the polymer composition comprises a branched ultraviolet radiation absorbing polyether that is not hyperbranched. In another embodiment, the polymer composition is substantially free of hyperbranched ultraviolet radiation absorbing polyethers (e.g., includes less than about 1% by weight of hyperbranched ultraviolet radiation absorbing polyether, such as less than about 0.1% by weight, such as completely free of hyperbranched ultraviolet radiation absorbing polyethers.

According to certain embodiments, the linear ultraviolet radiation absorbing polyether includes either or both of the repeat units shown in FIG. IA and FIG. IIB, below:

FORMULA IA. REPEAT UNIT OF LINEAR
POLYETHER UV ABSORBING POLYMER

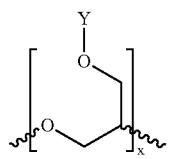

-continued
FORMULA IIB. REPEAT UNIT OF LINEAR
POLYETHER UV ABSORBING POLYMER

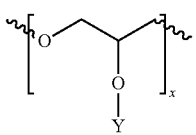

In FORMULAS IA and IIB, Y represents a UV-chromophore, as described below.

An illustrative example of a linear ultraviolet radiation absorbing polyether that comprises a chemically bound UV-chromophore is shown in FORMULA IIIC.

FORMULA IIIC. LINEAR
POLYETHER UV ABSORBING POLYMER

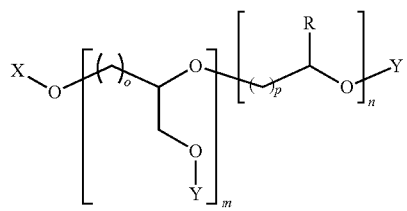

In the structure illustrated in FORMULA IIIC, X is either a terminal functional group or part of the polymer backbone; R is a pendant group attached to the polymer backbone, and X is a terminal group.

X and R may either be the same or different. X and R may be independently selected from, for example, hydrogen, linear alkyl, alkenyl or alkynyl hydrocarbon chains, linear siloxanes, and the like. In one embodiment the group X represents octadecane. Y represents a UV-chromophore and the groups represented by Y are described below. The proportion of ether repeat units bearing substituent Y is a real number expressed by Equation 1, $$\frac{m}{n+m} \qquad \text{Equation 1}$$

where m and n both represent a real number between 0 and 1, and the sum of n and m equals 1. In one embodiment, the number m=1 and n=0 (the polymer is a homopolymer and includes the repeat unit of FORMULA IA). In another embodiment, the number m<1 (the polymer is a copolymer) with R and Y pendant groups. For copolymers containing both R and Y pendant groups, the distribution of the pendant R and Y groups along the polymer chain can be modified to obtain optimal polymer properties. In one embodiment, the polymer is a random copolymer, and the groups R and Y are statistically distributed along the polymer chain. In another embodiment, the polymer is a block copolymer, consisting of alternating segments of polymer backbone functionalized with a greater proportion of either R or Y. In another embodiment, the distribution of the pendant groups R and Y along the polymer backbone is somewhere between the boundary conditions of block and statistically random copolymers. In FORMULA IIIC, the integers o and p represent the number of $CH_2$ groups in the repeat units bearing Y and R.

Introduction of varied R pendant groups can be achieved through the use of other co-monomers during the polymerization reaction. The size, chemical composition, weight percent and position in the backbone of these co-monomers can be varied to change the physical and chemical properties of the final polymer. Examples of co-monomers that can be incorporated into the polymer include, but are not limited to, ethylene oxide, propylene oxide, and glycidyl ethers such as n-butyl glycidyl ether, 2-ethylhexylglycidyl ether.

It is clear to one skilled in the art that polyethers of the type illustrated in FORMULAS IA, IIB and IIIC can be obtained through various synthetic routes; among these routes is ring-opening polymerization of cyclic ether monomers and optional co-monomers. The size of the ring in the cyclic ether monomers determines the values of o or p, and the resulting backbone structure of the polyether polymer. For monomers or co-monomers that are epoxides (three-membered rings containing two carbon atoms and one oxygen atom), the value of o or p in the resulting UV absorbing polyether is 1. A repeat unit that results from using an epoxide co-monomer is shown in structure A of FORMULA IV. For (co)monomers that are oxetanes (four-membered rings containing three carbon atoms and one oxygen atom), the value of o or p in the resulting UV absorbing polyether is 2. A repeat unit that results from using an oxetane co-monomer is shown in structure B of FORMULA IV. The length of the alkyl chain within each monomer type can be selected to modify the properties of the polymer. In one embodiment, both o and p equal 1. An example of this case is if the repeat units bearing Y and R are both derived from epoxide monomers (o=p=1), or both derived from oxetane monomers (o=p=2). In another embodiment, o and p are not equal. An example of this case is if the repeat units bearing the UV-chromophore Y are based on an epoxide monomer (o=1), and the repeat units bearing the group R are based on an oxetane monomer (p=2).

FORMULA IV. OPTIONAL REPEAT UNITS

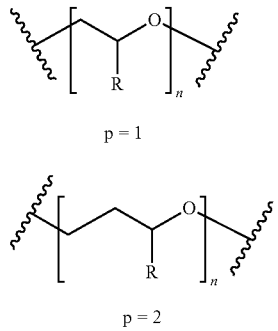

Suitable UV-chromophores that may be chemically bound in UV absorbing polyethers of the present invention include UV absorbing triazoles (a moiety containing a five-membered heterocyclic ring with two carbon and three nitrogen atoms), such as benzotriazoles. In another embodiment, the structure represented by Y contains or has a pendant UV absorbing triazine (a six membered heterocycle containing three nitrogen and three carbon atoms). Suitable UV-chromophores include those that have absorbance of UVA radiation; other suitable UV-chromophores are those which have absorbance in the UVB region. In one embodiment, the UV-chromophore absorbs in both the UVA and UVB region. In one embodiment, when the UV-absorbing polyether is cast into a film, it is possible to generate a molar extinction coefficient measured for at least one wavelength in this wavelength range of at least about 1000 $mol^{-1}$ $cm^{-1}$, preferably at least about 2000 $mol^{-1}$ $cm^{-1}$, more preferably at least about 4000 $mol^{-1}$ $cm^{-1}$. In one embodiment, the molar extinction coefficient among at least 40% of the wavelengths in this portion of the spectrum is at least about 1000 $mol^{-1}$ $cm^{-1}$. Examples of UV-chromophores that are UVA absorbing include triazoles such as benzotriazoles, such as hydroxyphenyl-benzotriazoles; camphors such as benzylidene camphor and its derivatives (such as terephthalylidene dicamphor sulfonic acid); dibenzoylmethanes and their derivatives.

In one embodiment, the UV-chromophore is a benzotriazole providing both photostability and strong UVA absorbance with a structure represented in FORMULA V.

FORMULA V. BENZOTRIAZOLE
UV ABSORBING CHROMOPHORE

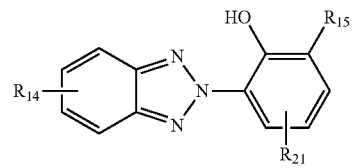

wherein each $R_{14}$ is independently selected from the group consisting of hydrogen, $C_1$-$C_{20}$ alkyl, alkoxy, acyl, alkyloxy, alkylamino, and halogen; $R_{15}$ is independently selected from the group consisting of hydrogen, $C_1$-$C_{20}$ alkyl, alkoxy, acyl, alkyloxy, and alkylamino, $R_{21}$ is selected from $C_1$-$C_{20}$ alkyl, alkoxy, acyl, alkyloxy, and alkylamino. Either of the $R_{15}$ or $R_{21}$ groups may include functional groups that allow attachment to a polymer. Compounds resembling the structure in FORMULA V are described in U.S. Pat. No. 5,869,030, and include, but are not limited to, methylene bis-benzotriazolyl tetramethylbutylphenol (a compound sold under the trade name TINSORB M by BASF Corporation, Wyandotte, Mich.). In one embodiment, the UV absorbing triazole is derived from a transesterification product of 3-(3-(2H-benzo[d][1,2,3]triazol-2-yl)-5-(tert-butyl)-4-hydroxyphenyl)propanoic acid with polyethylene glycol 300, commercially available as TINUVIN 213, also available from BASF. In another embodiment, the UV absorbing triazole is Benzenepropanoic acid, 3-(2H-benzotriazol-2-yl)-5-(1,1-dimethylethyl)-4-hydroxy-, $C_{7-9}$-branched and linear alkyl esters, commercially available as TINUVIN 99, also available from BASF. In another embodiment, the UV absorbing group contains a triazine moiety. An exemplary triazine is 6-octyl-2-(4-(4,6-di([1,1'-biphenyl]-4-yl)-1,3,5-triazin-2-yl)-3-hydroxyphenoxy)propanoate (a compound sold under the trade name TINUVIN 479 by BASF Corporation, Wyandotte, Mich.).

In another embodiment, the UV-chromophore is a UVB absorbing moiety. By UVB absorbing chromophore it is meant that the UV-chromophore has absorbance in the UVB portion (290 to 320 nm) of the ultraviolet spectrum. In one embodiment, the criteria for consideration as a UVB absorbing chromophore is similar to those described above for an UVA absorbing chromophore, except that the wavelength range is 290 nm to 320 nm. Examples of suitable UVB absorbing chromophores include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; benzalmalonate (benzylidene malonate); benzimidazole derivatives (such as phenyl benzilimazole sulfonic acid, PBSA), benzoxazole derivatives, and other suitably functionalized species capable of copolymerization within the polymer chain. In another embodiment, the UV-absorbing polyether includes more than one UV-chromophore or more than one chemical class of UV-chromophore.

UV-absorbing polyethers of the present invention may be synthesized by, according to certain embodiments, ring-opening polymerization of a suitable cyclic ether monomer to form a polyether, followed by covalent attachment of UV-chromophores to pendant functional groups ("post-polymerization attachment"). According to certain other embodiments, the UV-absorbing polyethers may be synthesized by polymerization of a cyclic ether monomer, wherein the monomer itself includes a covalently attached UV-chromophore (i.e., "direct polymerization").

Furthermore, as one skilled in the art will recognize, the synthesis of the UV absorbing polyether generally results in a reaction product that is polymer composition that is a mixture of various molecular weights of UV absorbing polyethers. In certain other embodiments, the reaction product may further include (apart from the polymer composition) a small amount of unpolymerized material which may be removed using techniques known in the art.

According to certain embodiments, the polymer composition has a low polydispersity. For example, the polydispersity index of the polymer composition may be about 1.5 or less, such as about 1.2 or less. Polydispersity index is defined as $M_w/M_N$ (i.e., the ratio of weight average molecular weight, $M_w$ to number average molecular weight, $M_N$). According to certain other embodiments, the polymer composition includes 50% or more by weight of a particular polymer molecule.

Polydispersity of the polymer composition may be kept low using, for example, particular synthetic procedures, such as ring-opening polymerization of a cyclic ether monomer and deprotection (described below). Alternatively or in addition, the polymer composition may be treated using techniques known in the art, such as solvent extraction and or using supercritical $CO_2$ to purify either the polyether prior to post-polymerization attachment or to purify the final polymer composition (e.g., after attachment of UV-chromophore).

Synthesis of the polymer by post-polymerization attachment of the UV-chromophore may include the steps of ring-opening polymerization of a cyclic ether monomer to form a polyether having protected groups; deprotecting the polyether to remove at least some of the protected groups; and attaching a UV-chromophore to the deprotected UV-absorbing polyether to form a UV-absorbing polyether having a chemically bound UV chromophore.

An example of post-polymerization attachment is illustrated schematically in FORMULA VI. An initiator I is used to induce polymerization of cyclic ether monomer M, generating polymer $P_0$ wherein pendant hydroxy functional groups are protected with a protecting group (P). Polymer $P_0$ is subjected to conditions that remove protecting group P, affording deprotected polymer $P_d$. Finally, UV-chromophore Y is attached to the pendant hydroxyl groups of polymer $P_d$, affording the desired final polymer, $P_f$.

FORMULA VI. SYNTHESIS OF UV ABSORBING CHROMOPHORE
BY POST-POLYMERIZATION FUNCTIONALIZATION

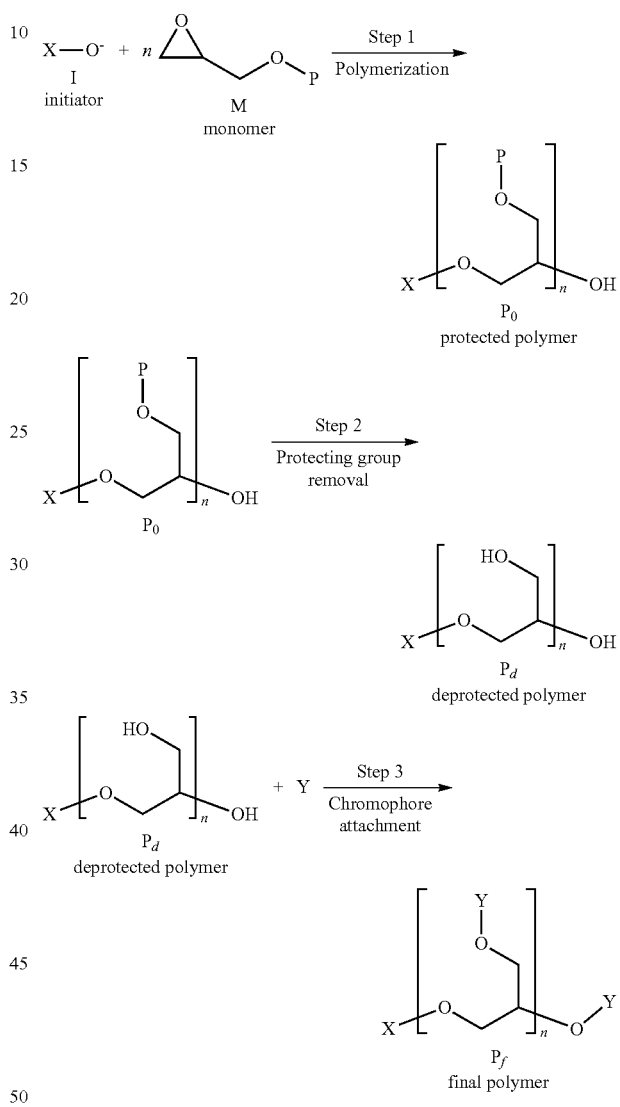

Ring-opening polymerization of cyclic ethers such as monomer M in FORMULA VI can be achieved using various methods including cationic and anionic ring-opening polymerization. In one embodiment, the polymerization is performed by anionic ring opening polymerization. Monomer M in FORMULA VI is a form of glycidol wherein the primary hydroxy group has been masked with protecting group P. Polymerization of unprotected glycidol results in the formation of highly branched polymers (U.S. Pat. No. 7,988,953B2, Tokar, R. et. al. *Macromolecules* 1994, 27, 320-322: Sunder, A. et. al. *Macromolecules* 1999: 4240-4246. Rokicki, G. et. al. *Green Chemistry* 2005, 7, 529). Conversely, anionic polymerization of glycidol derivaties where the primary hydroxyl group has been protected can generate linear polyethers, as illustrated by structure $P_0$ in FORMULA VI (Taton, D. et. al. *Macromolecular Chemistry* and *Physics* 1994, 195, 139-148: Erberich, M. et. al. *Macromolecules* 2007, 40, 3070-3079: Haouet, A. et. al. *European Polymer Journal* 1983, 19, 1089-1098: Obermeier, B. et. al *Bioconjugate Chemistry* 2011, 22, 436-444: Lee, B. F. et. al. *Journal of polymer science. Part A, Polymer chemistry* 2011, 49, 4498-4504). The protected cyclic ether monomer is not limited to epoxide derivates, and includes functionalized cyclic ethers containing 3 through 6 contiguous atoms; in another embodiment, the monomer M is an oxetane derivative containing a protected primary hydroxyl group.

By protected, it is meant that a functional group in a multifunctional molecule has been selectively derivatized with a moiety that prevents covalent modification at that functional group. Moieties that are used as protecting groups are typically attached to the desired functional groups with excellent chemical yield, and can be selectively removed as required in good yield, revealing the original functional group. Hydroxyl protecting groups include but are not limited to ethers such as methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), t-butoxymethyl, 4-pentenyloxymethyl (POM), siloxymethyl, 2-methoxyethoxymethyl (MEM), 2,2,2-trichloroethoxymethyl, bis(2-chloroethoxy) methyl, 2-(trimethylsilyl)ethoxymethyl (SEMOR), tetrahydropyranyl (THP), allyl, 3-bromotetrahydropyranyl, tetrahydrothiopyranyl, 1-methoxycyclohexyl, benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, trimethylsilyl (TMS), triethylsilyl (TES), trii sopropylsilyl (TIPS), t-butyldimethylsilyl (TBDMS), t-butyldiphenylsilyl (TBDPS), tribenzylsilyl, esters such as formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), and carbonates such as alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate. In one embodiment, the protecting group is ethoxyethyl ether; in another embodiment, the protecting group is allyl ether.

Removal of protecting groups from the protected linear polyether $P_0$ to generate deprotected polymer $P_d$ is achieved using methods complimentary to the choice of protecting group P; such methods are familiar to those skilled in the art. In one embodiment, the primary hydroxyl group of the cyclic ether monomer is protected as the 1-ethoxyethyl ether; the cleavage of this protecting group to generate the deprotected polymer is achieved using aqueous acidic conditions such as aqueous acetic acid, aqueous hydrochloric acid, or acidic ion exchange resin. In another embodiment, the primary hydroxyl group of the cyclic ether monomer protected as an allyl ether; the cleavage of this protecting group to generate the deprotected polymer is achieved by isomerizaion of the allyl ether to the vinyl ether by treatment with potassium alkoxide followed by treatment with aqueous acid, isomerization using transition metal catalysts followed by acidic hydrolysis, or direct removal using palladium (0) catalysts and a nucleophilic scavenger.

The anionic ring-opening polymerization of monomer M illustrated in FORMULA VI is initiated by alkoxide salt I. Examples of alkoxides suitable for initiation of ring-opening polymerization of cyclic ether monomers include, but are not limited to the potassium salts of linear C3 through C30 hydrocarbon alcohols, polyethylene glycol methyl ether, and carbinol terminated polysiloxanes. In one embodiment, the initiator for anionic ring-opening polymerization is the potassium salt of octadecanol. Another embodiment of the current invention makes use of a multifunctional initiator including, but not limited to polyoxyalkylenes such as polyethylene glycol, polypropylene glycol or poly(tetramethylene ether) glycol; polyesters such as poly(ethyleneadipate), poly(ethylenesuccinate); copolymers that have both oxyalkylene and ester functionality in the backbone such as poly[di(ethylene glycol)adipate]; and lower molecular weight alcohols such as 1,4-butanediol, 1,6-hexanediol or neopentyl glycol.

Depending on the functional groups pendant from the polymer, chromophores can be covalently attached to the polymer backbone using a variety of methods known to those skilled in the art. The following methods are illustrative, and do not represent an exhaustive list of the possible means to attach a UV-chromophore to the polymer backbone. In the case of polymers with free hydroxyl groups (as represented by structure $P_d$ FORMULA VI) a UV-chromophore containing a carboxylate group may be covalently attached to the polymer using a number of methods familiar to those skilled in the art. Condensation reagents can be used to form covalent bonds between UV-chromophores with carboxylic acids and hydroxyl groups on polymers generating ester bonds; in one embodiment, the condensation reagent is N-(3-dimethylaminopropyl)-N'-ethylcarbodiimide hydrochloride. The carboxylic acid of the UV-chromophore may also be attached to hydroxyl groups on the polymer through ester bonds using transition metal catalysis; in one embodiment, the catalyst is tin (II) ethylhexanoate. The UV-chromophore can also be attached to the polymer by converting the carboxylic acid of the UV-chromophore to the corresponding acid chloride; the acid chloride reacts with hydroxyl groups on the functional polymer forming ester bonds; in one embodiment, this conversion to the acid chloride is performed using thionyl chloride. The UV-chromophore carboxylic acid may also be converted to the isocyanate through Curtius rearrangement of an intermediate acid azide; the chromophore isocyanate reacts with hydroxyl groups on the functional polymer forming a urethane bonds. In another embodiment, the carboxylic acid on the UV-chromophore can be converted to an ester, and attached to the hydroxyl group on the backbone by transesterification. This can be achieved by conversion of the carboxylic acid to an ester with a low boiling alcohol such as methanol; transesterification is performed by reacting the chromophore ester with the polymer containing side chain hydroxyl groups using an acid catalyst, for instance, paratoluene sulfonic acid.

In the case of polymers with free hydroxyl groups (as represented by structure $P_d$ in FORMULA VI) a UV-chromophore containing a hydroxyl group may be covalently attached to the polymer using a number of methods familiar to those skilled in the art. In one embodiment, the hydroxyl group on the UV-chromophore can be activated for nucleophilic displacement using a reagent such as methane sulfonyl chloride or p-toluene sulfonyl chloride; the hydroxyl groups on the backbone are then able to displace the resulting mesylate or tosylate under basic conditions to generate an ether bond between the polymer and the UV-chromophore. In another embodiment, the hydroxyl group on the UV-chromophore can be converted to the chloroformate using a reagent such as phosgene, diphosgene, or triphosgene; the resulting UV-chromophore chloroformate can react with hydroxyl groups on the backbone of the polymer to generate a carbonate bond between the polymer and the UV-chromophore.

In the case of polymers with free hydroxyl groups (as represented by structure $P_d$ in FORMULA VI) a UV-chromophore containing an amine group may be covalently attached to the polymer using a number of methods familiar to those skilled in the art. In one embodiment, the hydroxyl groups on the polymer can be converted to the corresponding chloroformates using a reagent such as phosgene, diphosgene and triphosgene; the amine functionalized UV-chromophore can then react with the polymer chloroformates generating a carbamate bond between the UV-chromophore and polymer.

In another embodiment, some of the hydroxyl groups on the linear polymer backbone remain after the acid, acid chloride or isocyanate functional UV-chromophores are attached. These unreacted hydroxyl groups may be used to attach other monofunctional side groups to improve the physical and chemical properties of the polymer. Examples of hydroxyl reactive functional groups include, but are not limited to, acid chlorides and isocyanates. Specific examples of hydroxyl reactive functional side groups include palmitoyl chloride and stearyl isocyanate. Other examples of groups that may be pendant from polymers that are sites for covalent attachment of UV-chromophores include, but are not limited to, conjugated alkenes, amines, and carboxylic acids.

In a another embodiment, the polyether backbone is a polyglycerol with pendant hydroxyl groups or hydrophobic groups, such as a polyglyceryl ester, for example, decaglyceryl monostearate sold under the tradename POLYALDO 10-1-S by Lonza in Allendale, N.J. or tetradecaglyceryl monostearate sold under the tradename POLYALDO 14-1-S by Lonza in Allendale, N.J. The pendant hydroxyl groups may be reacted with a UV-chromophore containing a complementary functional group as described above to obtain a UV absorbing polyether. In this embodiment, the polymer composition will be, for example, the reaction product of a polyglycerol ester and a UV chromophore having a functional group suitable for covalent attachment to said polyglycerol ester. Suitable functional groups on the UV chromophore include carboxylates, isocyanates, among other functional groups discussed previously. The resulting polymer composition may include a linear UV-absorbing polyether having the repeat unit shown in FORMULA IIB. The resulting polymer composition may further include some non-linear (e.g., cyclic components) as well, depending upon the percentage of linear material present in the polyglycerol.

As described above, the synthesis of functionalized polymers, such as those in FORMULA IIIC, could also be achieved through polymerization of UV-chromophores covalently modified with cyclic ether groups (direct polymerization). This is illustrated in FORMULA VII, where Y represents a UV-chromophore, and o is a characteristic of the ring size of the cyclic ether monomer.

As one skilled in the art will recognize the reaction product to make the UV-absorbing polyether may include not only the polymer composition, but may also include some unreacted/unpolymerized.

FORMULA VII. DIRECT POLYMERIZATION OF UV-CHROMOPHORE COVALENTLY ATTACHED TO CYCLIC ETHER

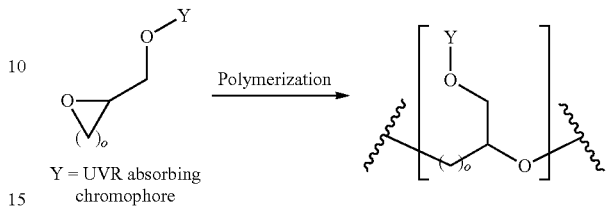

Y = UVR absorbing chromophore

The UV absorbing polymers described herein are useful in applications where UV absorption is desired. For example, the polymer may be useful for combining with a suitable cosmetically acceptable carrier for cosmetic applications or combining the UV absorbing polymer with other materials to reduce UV degradation of the materials (i.e., melt blending the material with the UV absorbing polymer or coating the material with the UV absorbing polymer). The incorporation of polymers of the present invention into such compositions may provide enhanced SPF (primarily UVB absorbance), enhanced PFA (primarily UVA absorbance) or enhancement of both. The cosmetically-acceptable topical carrier is suitable for topical application to human skin and may include for example, one or more of vehicles such as water, ethanol, isopropanol, emollients, humectants, and/or one or more of surfactants/emulsifiers, fragrances, preservatives, water-proofing polymers, and similar ingredients commonly used in cosmetic formulations. As such, the UV absorbing polymer may be formulated using ingredients known in the art into a spray, lotion, gel, stick or other product forms. Similarly, according to certain embodiments, one may protect human skin from UV radiation by topically applying a composition comprising the UV absorbing polymer.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Synthesis of a Protected Form of glycidol

FORMULA VIII. SYNTHESIS OF PROTECTED EPOXIDE MONOMER

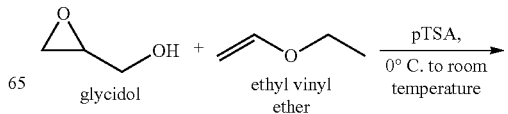

-continued

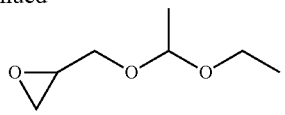

1
2,3-epoxypropyl-
1-ethoxyethyl ether

The synthesis of protected epoxide monomer 1 was performed as illustrated in FORMULA VIII using a variation of a procedure described in the literature (Fitton, A. et. al. *Synthesis* 1987, 1987, 1140-1142). Glycidol (53 mL, 0.80 moles) and ethyl vinyl ether (230 mL, 2.40 moles; distilled immediately before reaction) were added to a 2-neck 500 mL round bottom flask containing a magnetic stir bar. The flask was fitted with a septum and thermometer adapter; a thermometer was inserted into the adapter and positioned such that the bulb was immersed in the liquid. The flask was immersed in a brine/ice bath; the mixture was magnetically stirred. When the internal temperature was 0° C., p-toluene sulfonic acid hydrate (pTSA.H$_2$O, 1.43 g, 7.5 mmol) was added in small portions while stirring vigorously. On addition of each portion of pTSA, the temperature of the solution increased sharply; the rate of addition was slow enough to prevent the solution temperature increasing above 20° C. The final portion of pTSA was added ~5 hours after addition of the initial portion, and resulted in no exotherm; thin layer chromatography of the reaction mixture revealed no residual glycidol following the final pTSA addition. The reaction mixture was transferred into a separatory funnel; saturated aqueous NaHCO$_3$ (230 mL) was poured into the funnel slowly. The mixture was shaken, the layers allowed to separate, and the organic layer was removed, dried over sodium sulfate, and filtered through paper. The solution was concentrated by rotary evaporation, then vacuum distilled (60° C. distillate at 8 torr) affording protected epoxide monomer 1 (79.38 g) as a clear oil. NMR analysis was performed on a Varian Unity Inova 400 MHz spectrometer ($^1$H) spectrometer at 30° C.; chemical shifts are reported in parts per million (ppm) on the δ scale, and were referenced to residual protonated solvent peaks or tetramethylsilane. Spectra obtained in DMSO-d$_6$ were referenced to (CHD$_2$) (CD$_3$)SO at δ$_H$ 2.50. $^1$H NMR (400 MHz, CDCl$_3$) δ ppm 4.76 (quin, J=5.2 Hz, 1 H), 3.81 (dd, J=11.5, 3.3 Hz, 1 H), 3.60-3.74 (m, 3 H), 3.38-3.60 (m, 4 H), 3.10-3.20 (m, 2 H), 2.81 (ddd, J=5.1, 4.0, 1.3 Hz, 2 H), 2.63 (ddd, J=14.6, 5.1, 2.7 Hz, 2 H), 1.33 (dd, 5.4 Hz, 6 H), 1.21 (td, J=7.1, 1.3 Hz, 6 H).

Example 2A

Synthesis of Linear polyglycerol

FORMULA IX. SYNTHESIS OF LINEAR POLYETHER POLYMER

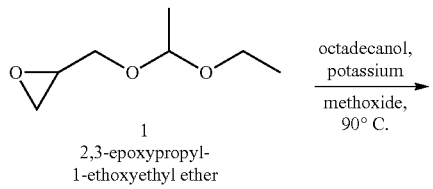

1
2,3-epoxypropyl-
1-ethoxyethyl ether octadecanol,
potassium
methoxide,
90° C.

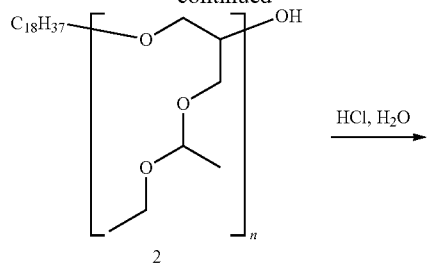

2

HCl, H$_2$O
→

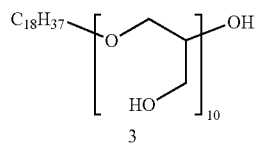

3

Polymerization of protected epoxide monomer 1 was achieved as illustrated in FORMULA IX. 1-Octadecanol (27.76 g, 102.6 mmol) was added to an oven-dried 250 mL 2-neck round bottom flask containing a magnetic stir bar. The flask was fitted with a nitrogen inlet adapter and rubber septum. Potassium methoxide (25 wt % in methanol (MeOH), 6.06 mL, 20.52 mmol) was added to the flask by syringe through the septum. The round bottom flask was immersed in an oil bath which had been pre-heated to 90° C. The septum was pierced with an 18 gauge needle, and the material in the flask was stirred under a constant stream of nitrogen gas for 1 hour, during which time the alcohol melted, and methanol evaporated from the flask. The septum was replaced with a pressure equalizing addition funnel containing monomer 1 (151 g, 1.04 moles). The funnel was sealed with a rubber septum. The monomer 1 was added dropwise to the stirred mixture; the reaction mixture was stirred at 90° C. for 15 hours. On cooling, this afforded crude polyether 2 as a pale brown, slightly viscous oil that was used in subsequent reactions without further purification. $^1$H NMR (400 MHz, CHLOROFORM-d) δ ppm 4.48-4.80 (m, 10 H), 3.25-3.97 (m, 70 H), 1.41-1.64 (m, 2 H), 1.23-1.40 (m, 60 H), 1.09-1.23 (m, 30 H), 0.88 (t, J=7.0 Hz, 3 H).

Gel permeation chromatography for molecular weight determination was performed at 35° C. on a Waters Alliance 2695 Separations Module (Waters, Milford, Mass.) at a flow rate of 0.5 mL/min THF (stabilized w/0.025% BHT). The 2695 was equipped with two GPC columns in series (Waters Corp HR 0.5 and HR3) with dimensions of 7.8×300 mm with 5 μm particle size) and a Waters model 410 refractive index detector. The molecular weights of the samples were determined by comparison to polystyrene standards. Standards were prepared by weighing 1-2 mg of each polystyrene (PS) polymer into a 2 mL vial with THF solvent (2 standards per vial); samples were filtered (0.22 μm) prior to analysis. Polystyrene standards spanned a range between 70,000 to 600 Daltons, and were manufactured by three vendors (Polymer Standards Service-USA, Phenomenex and Shodex). The resultant calibration curve provided an r$^2$=0.9999. Experimental samples were dissolved in THF at a concentration of 3-5 mg/mL and filtered (0.22 μm) prior to analysis. GPC (THF) analysis for polymer 2: M$_w$ 1724.

Crude polyether 2 was transferred with tetrahydrofuran (THF, ~500 mL) into a 1 L round bottom flask containing a magnetic stir bar. Concentrated aqueous HCl (37%, 20 mL) was added to the stirred reaction mixture by glass pipette. After 16 hours, the reaction mixture was concentrated by rotary evaporation to an oil which was diluted with methanol to ~500 mL. Solid NaHCO$_3$ was added in portions to the vigorously stirred solution, causing significant bubbling. When addition of the $NaHCO_3$ did not produce further bubbling (total $NaHCO_3$ added was 107 g) the mixture was filtered through paper to remove solid $NaHCO_3$. The filtrate was concentrated by rotary evaporation affording linear polyglycerol 3 as a tan foam. $^1$H NMR (400 MHz, DMSO-$d_6$) δ ppm 4.43 (br. s., 11 H), 3.20-3.70 (m, 52 H), 1.38-1.55 (m, 2 H), 1.23 (s, 30 H), 0.85 (t, J=7.0 Hz, 3 H).

Example 2B

Synthesis of Linear polyglycerol

A different batch of protected crude polymer 2 (260 g) and methanol (ACS grade, 1.25 L) was transferred into a 2 L 2-neck round bottom flask. Dry, $H^+$ form acidic ion-exchange resin in (Dowex DR-2030 from Aldrich, 446483; 100.3 g) was added to the flask. The center neck of the flask was fitted with an adapter for mechanical stirring and a paddle; the side neck of the flask was fitted with a water cooled distillation adapter. The reaction flask was immersed in an oil bath. With vigorous mechanical stirring, the reaction mixture was heated to boiling (oil bath temperature of 85° C.). Methanol (and the methyl ether resulting from removal of the protecting groups) was distilled from the flask. After 750 mL of methanol were collected, an additional portion of methanol (750 mL) was added to the reaction mixture. Another 750 mL of methanol was allowed to distill from the flask. Decolorizing charcoal was added to the hot reaction mixture. The mixture was stirred briefly and then filtered through paper. The filtrate was concentrated by rotary evaporation. Residual solvent was removed under vacuum affording the final linear polyglycerol as a yellowish foam (107 g).

Example 3A

Synthesis of benzotriazole chromophore carboxylate

FORMULA X. BENZOTRIAZOLE CABOXYLATE

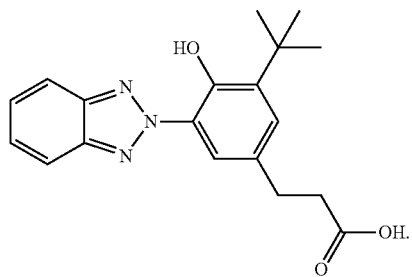

The polyethylene glycol ester of 3-[3-(2H-1,2,3-benzotriazol-2-yl)-5-tert-butyl-4-hydroxyphenyl]propanoate (a chromophore sold under the trade name TINUVIN 213 by BASF Corporation, Wyandotte, Mich.) (81.0 g) was added to a 2 L round bottom flask containing a magnetic stir bar. EtOH (600 mL) was added to the flask by funnel, and the mixture was stirred until homogeneous. Sodium hydroxide (NaOH, 30.8 g) was dissolved in $H_2O$ (400 mL); the basic solution was transferred into an addition funnel above the 2 L flask. The NaOH solution was added slowly to the stirred mixture; the pale amber cloudy solution immediately turned clear and dark orange. When addition was complete, the mixture was stirred overnight at room temperature. The solution was concentrated by rotary evaporation to remove most of the EtOH. The resulting orange oil was diluted to 1400 mL with $H_2O$. The mixture was stirred mechanically and was acidified to ~pH 1 by addition of 1 M aq. HCl (~700 mL). The resulting white precipitate was filtered and pressed to remove water, then recrystallized from EtOH. The first crop of crystals were long, thin colorless needles. The supernatant was removed and concentrated by rotary evaporation; a second crop of material was isolated as a white, amorphous solid. The two crops were combined and dried in a vacuum oven overnight affording a UV-chromophore having a carboxylate group, specifically benzotriazole carboxylate 4, 3-(3-(2H-benzo[d][1,2,3]triazol-2-yl)-5-(tert-butyl)-4-hydroxyphenyl) propanoic acid (37.2 g) as a white solid; the structure is illustrated in FORMULA X. $^1$H NMR (400 MHz, DMSO-$d_6$) δ ppm 11.25 (br. s, 1 H), 8.00-8.20 (m, 2H), 7.95 (d, J=2.1 Hz, 1 H), 7.50-7.67 (m, 2 H), 7.28 (d, J=2.1 Hz, 1 H), 2.87 (t, J=7.5 Hz, 2 H), 2.56 (t, J =7.5 Hz, 2 H), 1.45 (s, 9 H).

Example 3B

Synthesis of benzotriazole chromophore carboxylate

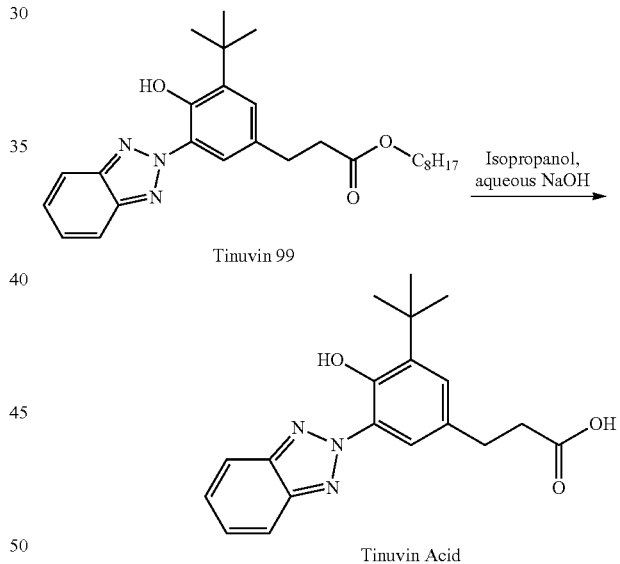

Benzenepropanoic acid, 3-(2H-benzotriazol-2-yl)-5-(1,1-dimethylethyl)-4-hydroxy-, C7-9-branched and linear alkyl esters, commercially available as TINUVIN 99 from BASF (120 g, 265.7 mmol) was added to a 3 L single neck round bottom flask containing a magnetic stir bar. Isopropanol (900 ml, ACS grade) was added to the flask, and the resulting mixture was stirred until complete dissolution. Sodium hydroxide (36 g, 900 mmol) was dissolved in 600 ml of distilled water, and the solution was added to the reaction mixture. The resulting opaque mixture, which in 40 min became a clear orange solution, was stirred at room temperature for 24 hours, and then slowly added to a vigorously stirred mixture of isopropanol (1800 ml, ACS grade) and 1N HCl (1200 ml), cooled to 10-15° C. The precipitated white solid was filtered, washed with 1.2 L of 1:1 isopropanol-1N HCl mixture, suspended in 2 L of 0.25N HCl, stirred for 1 hour, filtered and dried at 90° C. in a vacuum oven overnight. The resulting UV-chromophore having a carboxylate group, specifically a benzotriazole carboxylate 4 (37.2 g) was obtained as a pale yellow solid, 85 g, 94.5%.

Example 4

Esterification of polyether Backbone with benzotriazole carboxylate

FORMULA XI. ESTERIFICATION OF POLYGLYCEROL WITH BENZOTRIAZOLE CARBOXYLATE

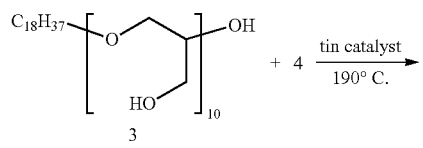
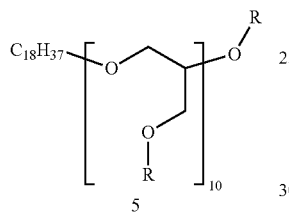
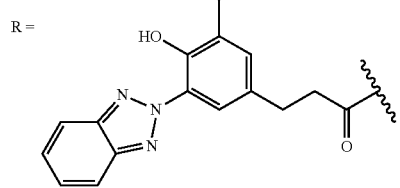

FORMULA XI illustrates the esterification of polyglycerol 3 with benzotriazole carboxylate 4 using catalytic tin. Linear polyglycerol 3 of Example 2A (5.52 g, 60.1 hydroxyl milliequivalents) was dissolved in methanol and transferred into a 500 mL 2-neck round bottom flask. The methanol was removed using rotary evaporation; benzotriazole carboxylate 4 (20.38 g, 60.1 mmol)) and a magnetic stir bar were added to the flask. The flask was fitted with a nitrogen inlet adapter and vacuum distillation adapter with 100 mL receiving flask. The flask was placed under vacuum (<1 Torr) for 1 hour, then backfilled with nitrogen gas. The inlet adapter was removed from the 500 mL flask; tin (II) ethyl hexanoate (49 µL, 0.15 mmol) was added to the flask by syringe under a stream of nitrogen. The apparatus was reassembled and immersed in an oil bath pre-heated to 200° C. When most of the solid had melted, the oil bath was cooled to 190° C. The reaction was stirred under a flow of nitrogen for 16 hours. While maintaining temperature and stirring, the reaction flask was then placed under vacuum (<1 Torr) for an additional 24 hours. The apparatus was then backfilled with nitrogen and cooled to room temperature. The material was freeze fractured and ground to powder using a mortar and pestle. The powder was dissolved in a minimal amount of THF. Methanol (900 mL) and a magnetic stir bar were added to an Erlenmeyer flask; the flask was immersed in an ice bath. The THF solution was added to the methanol with vigorous stirring; the resulting precipitate was isolated by vacuum filtration. Residual solvent was removed under vacuum overnight, affording the linear polyglycerol 5 (18.7 g) as an off-white solid. $^1$H NMR (400 MHz, CDCl$_3$) δ ppm 11.71 (br. s., 9 H), 8.03 (br. s., 9 H), 7.80 (br. s, 18 H), 7.28-7.48 (m, 18 H), 7.12 (br. s, 9 H), 5.19 (br. s, 1 H), 3.98-4.46 (br. m, 20 H), 3.21-3.61 (br. m, 32 H), 2.91 (br. s, 18 H), 2.67 (br. s, 18H), 1.38-1.51 (m, 85 H), 1.13-1.35 (m, 28 H), 0.87 (t, J=6.6 Hz, 3 H). GPC (THF): $M_w$ 3299; $M_n$ 2913.

Example 5

Conversion of benzotriazole arboxylate to acid chloride (3-(3-(2H-benzo[d] [1,2,3]triazol-2-yl)-5-(tert-butyl)-4-hydroxyphenyl)propanoyl chloride)

FORMULA XII. CONVERSION OF BENZOTRIAZOLE CARBOXYLATE TO BENZOTRIAZOLE ACID CHLORIDE

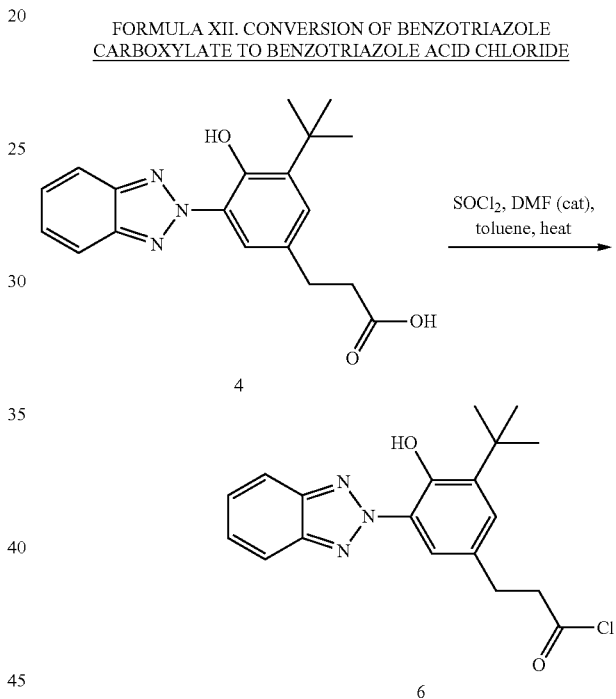

The conversion of the benzotriazole carboxylic acid 4 to the corresponding benzotriazole acid chloride 6 is illustrated in FORMULA XII. Benzotriazole carboxylate 4 (50 g 147 mmol, synthesized as described in Example 3 was added to a 1000 mL 3-neck flask containing a magnetic stir bar; the flask was equipped with a reflux condenser, nitrogen inlet, and rubber septum. Anhydrous toluene (~500 mL) was transferred into the flask by cannula through the septum. Thionyl chloride (16.1 mL, 221 mmol) was transferred into the flask by syringe; dimethylformamide (2.7 mL) was then added to the flask by syringe. The flask was immersed in an oil bath set at 80° C.; the suspension was stirred; the solids began to disperse, eventually yielding a clear solution. After ~4 hours, the reaction mixture was allowed to cool, transferred to a round bottom flask and concentrated by rotary evaporation. The resulting oil was triturated with hexanes, affording a beige solid. The suspension of material was recrystallized by adding additional hexanes and warming to reflux, filtration through paper, and slow cooling to room temperature with stirring. The resulting beige crystals were filtered and dried under vacuum at 50° C. The filtrate was concentrated, and the recrystallization performed a second time affording a second crop of crystals; the mass of the combined crops of benzotriazole acid chloride 6 was 44.7 grams. $^1$H NMR (400 MHz, CDCl$_3$) δ 11.88 (s, 1 H), 8.16 (d, J=2.2 Hz, 1 H), 7.91-7.98 (m, 2 H), 7.47-7.54 (m, 2 H), 7.21 (d, J=2.2 Hz, 1 H), 3.29 (t, J =7.5 Hz, 2 H), 3.07 (t, J=7.5 Hz, 2 H), 1.50-1.53 (s, 9 H).

Example 6

Conversion of benzotriazole acid chloride to isocyanate (2-(2H-benzo[d][1,2,3]triazol-2-yl)-6-(tert-butyl)-4-(2-isocyanatoethyl)phenol)

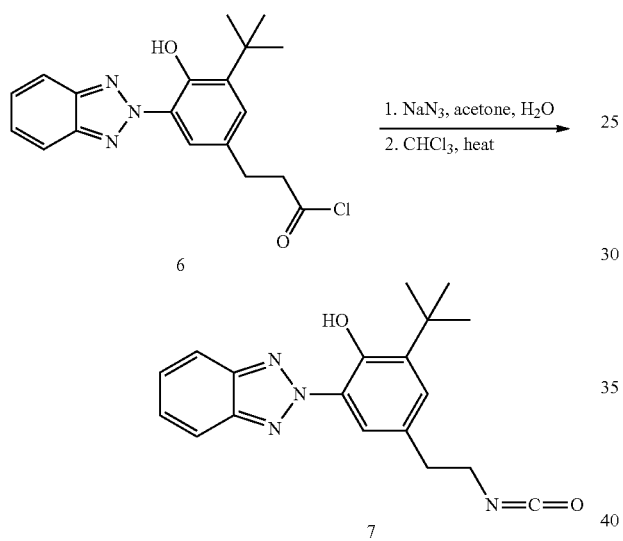

FORMULA XIII. CONVERSION OF ACID CHLORIDE TO ISOCYANATE

Synthesis of a benzotriazole isocyanate 7 suitable for coupling to pendant functional groups is illustrated in FORMULA XIII Sodium azide (NaN$_3$, 2.5 g, 38 mmol: CAUTION! NaN$_3$ is a violent poison) was carefully transferred into a single necked 500 mL round bottom flask containing a magnetic stir bar. Deionized water (20 mL) was added to the flask; the NaN$_3$ dissolved with mixing affording a clear solution. The flask was immersed in an ice bath. Acid chloride 6 (7.0 g 20 mmol) and anhydrous acetone (45 mL) were transferred into a pressure equalizing addition funnel in a positive pressure N$_2$ atmosphere glove box. The acid chloride dissolved in the acetone with gentle swirling, affording a clear yellow solution. The addition funnel containing benzotriazole acid chloride 6 was fitted into the flask containing the aqueous solution of NaN$_3$; the top of the addition funnel was fitted with a N$_2$ adapter connected to a vacuum gas manifold. The solution of benzotriazole acid chloride 6 was added dropwise to the NaN$_3$ solution. After addition of several drops, a white precipitate began to appear, suspended in the aqueous solution. Addition of benzotriazole acid chloride 6 was complete within 30 minutes; mixing was continued for 20 minutes in the ice bath. Water (30 mL) was added to the resulting white slurry; solids were collected by filtration through a glass fritted funnel under vacuum. The white solid was transferred to a separatory funnel followed with CHCl$_3$ (185 mL). The flask was shaken and the layers were allowed to separate. The lower organic phase was removed from the small aqueous layer and dried over Na$_2$SO$_4$. The solution was filtered; the filtrate was placed in a single necked 500 mL round bottom flask containing a magnetic stir bar; the flask was fitted with a reflux condenser with nitrogen inlet adapter and immersed in an oil bath. The solution was heated slowly to reflux over 30 minutes. The final oil bath temperature was 65° C. As the oil bath temperature surpassed 55° C., bubbling was apparent in the solution. The reaction was allowed to reflux for a total of 90 min. CHCl$_3$ was then removed by rotary evaporation; the resulting oil crystallized overnight on standing affording the benzotriazole isocyanate 7 (5.8 g) as a slightly grey solid. $^1$H NMR (400 MHz, CDCl$_3$) δ 11.91 (s, 1 H), 8.18 (d, J=1.9 Hz, 1 H), 7.92-7.98 (m, 2 H), 7.47-7.53 (m, 2 H), 7.23 (d, J=2.1 Hz, 1 H), 3.59 (t, J=6.9 Hz, 2 H), 2.96 (t, J=6.9 Hz, 2 H), 1.52 (s, 9 H).

Example 7

Coupling of isocyanate to polyglycerol

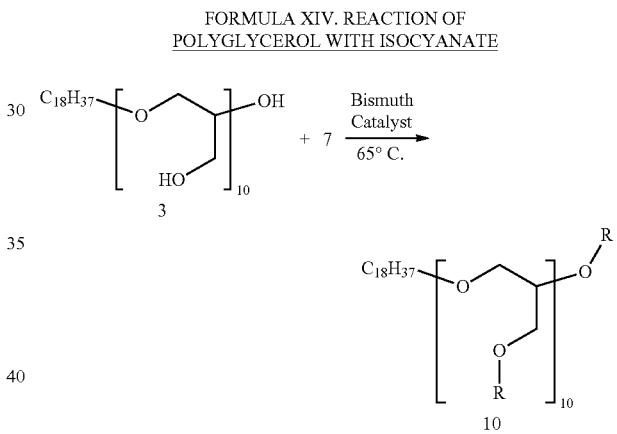

FORMULA XIV. REACTION OF POLYGLYCEROL WITH ISOCYANATE

R = 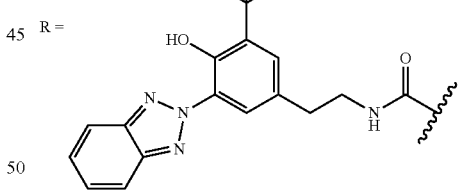

The reaction of linear polyglycerol 3 with benzotriazole isocyanate 7 is illustrated in FORMULA XIV. A solution of polyglycerol 3 in methanol was concentrated by rotary evaporation; residual solvent was removed in a vacuum oven overnight at 75° C. The polymer (2.22 g, 24.1 hydroxyl milliequivalents) was added to a 100 mL 2-neck round bottom flask containing a magnetic stir bar. Isocyanate 7 (7.65 g, 22.7 mmol), bismuth catalyst (25 mg; a bismuth carboxylate complex sold under the trade name BICAT 8210 by Shepherd Chemical, Norwood, Ohio) and THF (17.4 ml, dried over 3 angstrom molecular sieves) were added to the flask. The flask was placed in a 65° C. heated oil bath and fitted with a gas inlet. The reaction mixture was stirred for 5 hours under a nitrogen atmosphere, then allowed to cool to room temperature. FTIR was used to confirm the disappearance of the strong isocyanate peak at 2250 cm$^{-1}$. The reaction mixture was poured into 160 ml of methanol, resulting in a tan precipitate. Methanol was decanted off and the product was washed in the flask with methanol (2×75 mL). Residual solvent was removed in a vacuum oven overnight at 60° C.; the material was ground to a fine powder.

Example 8

Synthesis of an epoxide chromophore for the Direct Polymerization Method

FORMULA XV. SYNTHESIS OF
EPOXIDE CHROMOPHORE MONOMER

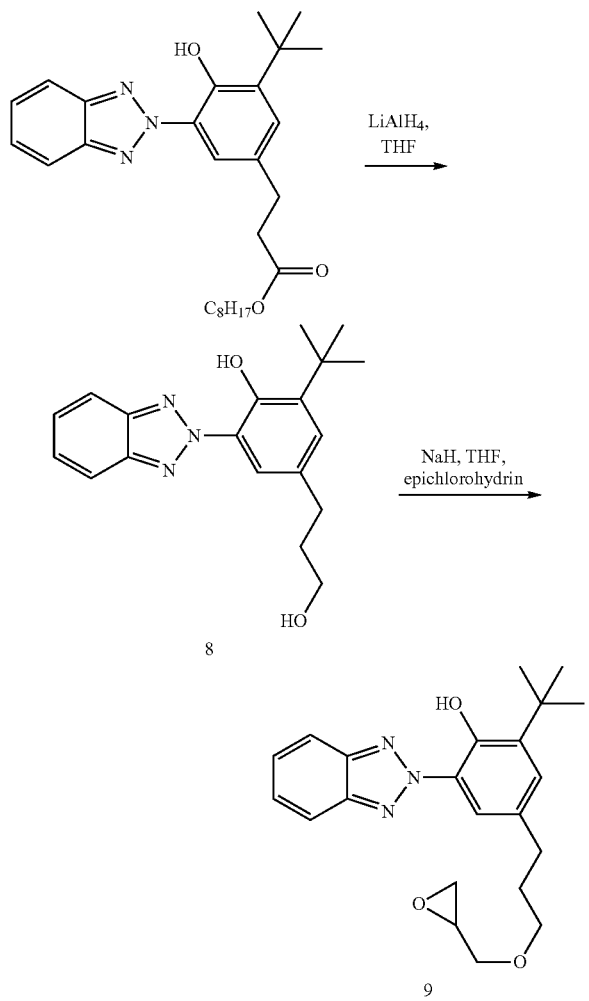

The synthesis of an epoxide monomer 9 bearing a benzotriazole chromophore is illustrated in FORMULA XV. A solution of lithium aluminum hydride (LAH) in THF (a 1 M, 250 mL) was transferred by cannula under nitrogen atmosphere into an oven-dried 500 mL 2-neck round bottom flask containing a magnetic stir bar and fitted with a rubber septum and pressure equalizing addition funnel. The reaction flask was immersed in an ice bath; stirring was started. Benzenepropanoic acid, 3-(2H-benzotriazol-2-yl)-5-(1,1-dimethylethyl)-4-hydroxy,C7-C9 branched and linear alkyl ester containing 5 wt. % 1-methoxy-2-propyl acetate (50.06 g; a benzotriazole UV absorbing product sold under the trade name TINUVIN 99-2 by BASF Corporation, Wyandotte, Mich.) was transferred into the addition funnel, and dissolved in anhydrous THF (30 mL). The THF solution containing the benzotriazole was added dropwise to the solution containing LAH; this resulted in slow fizzing. After the addition was complete, an additional portion of LAH solution (100 mL) was cannulated into the reaction flask. The reaction was allowed to warm to room temperature with stirring. After 2 hours, the reaction mixture was poured into a 1 liter erlenmeyer flask which was immersed in an ice bath. The solution was stirred mechanically while water (~60 mL) was added slowly to quench any residual LAH (EXTREME CAUTION: quenching of LAH with water is exothermic and releases large quantities of highly flammable H$_2$ gas). When the LAH was quenched (no additional gas released with additional water), the grey suspension was diluted to 1 L with 1 M aqueous HCl. This solution was transferred into a 2 L separatory funnel and extracted with ethyl acetate (1×400 mL, then 2×50 mL). The combined ethyl acetate layers were washed with brine (1×400 mL), dried over Na$_2$SO$_4$, then filtered through paper. Solvent was removed first by rotary evaporation and then in a vacuum oven overnight affording benzotriazol alcohol 8 (42.16 g) as a beige solid with a strong unpleasant odor. $^1$H NMR (400 MHz, CDCl$_3$) δ ppm 11.75 (s, 1 H), 8.15 (d, J=2.1 Hz, 1 H), 7.88-7.99 (m, 2 H), 7.43-7.52 (m, 2 H), 7.22 (d, J=2.1 Hz, 1 H), 3.75 (m, 2 H), 3.62 (br. s, 1 H), 2.77 (t, J=7.7 Hz, 2 H), 1.91-2.06 (m, 2 H), 1.52 (s, 9 H).

Sodium hydride (6.0 g, 250 mmol) was added to an oven-dried 3-neck round bottom flask containing a magnetic stirring bar. The flask was fitted with a pressure equalizing addition funnel, nitrogen inlet adapter and rubber septum. Anhydrous THF (300 mL) was added to the flask by cannula under nitrogen; the flask was then immersed in an ice bath, and stirring was starting. Benzotriazol Alcohol 8 (20.0 g, 61.5 mmol) and a small magnetic stirring bar were added to the addition funnel; THF was cannulated into the addition funnel, and the stir bar was agitated to promote dissolution of the alcohol in the THF. The final volume of the alcohol/THF solution was 65 mL. This solution was added dropwise to the cold, stirred sodium hydride suspension. The cold reaction mixture was stirred for 1 hour, then epichlorohydrin (20 mL, 256 mmol) was added by syringe through the septum. The addition funnel was exchanged with a reflux condenser with nitrogen inlet, and the round bottom flask was immersed in an oil bath at 70° C. The mixture was stirred for 19 hours, then the mixture was transferred to a separatory funnel with 1M aqueous HCl (750 mL) and ethyl acetate (500 mL). After shaking, the aqueous layer was discarded. The organic layer was washed with water (2×250 mL) and brine (1×250 mL) then dried over Na$_2$SO$_4$. The solution was concentrated by rotary evaporation. The crude product was purified by chromatography on silica gel (6:1 hexanes/ethyl acetate). Fractions containing the desired product were pooled, concentrated by rotary evaporation; residual solvent was removed under vacuum overnight affording the epoxide monomer 9 bearing a benzotriazole chromophore (7.35 g) as a beige solid . $^1$H NMR (400 MHz, CDCl$_3$) δ ppm 11.77 (s, 1 H), 8.14 (d, J=1.9 Hz, 1 H), 7.85-8.00 (m, 2 H), 7.41-7.53 (m, 2 H), 7.21 (d, J=1.9 Hz, 1 H), 3.74 (dd, J=11.5, 3.1 Hz, 1 H), 3.57 (ddt, J=19.8, 9.3, 6.4 Hz, 2 H), 3.43 (dd, J=11.5, 5.8 Hz, 1 H), 3.19 (ddt, J=5.8, 4.0, 2.9 Hz, 1 H), 2.82 (br. t, J=4.7 Hz, 1 H), 2.76 (br. t, J=7.7 Hz, 2 H), 2.64 (dd, J=5.1, 2.6 Hz, 1 H), 1.93-2.04 (m, 2 H), 1.52 (s, 9 H).

Example 9

Esterification of Alternate polyglycerol with benzotriazole acid

A polyglycerol partially esterified with stearic acid (2.5 g, 19.8 hydroxy milliequivalents; tetradecaglyceryl monostearate sold under the trade name POLYALDO 14-1-S by Lonza, Allendale, N.J.) and benzotriazole carboxylate 4 (8.8 g, 23.8 mmol) were transferred into a 2-neck 100 mL round bottom flask containing a magnetic stir bar. The flask was fitted with a nitrogen inlet adapter and distillation adapter with 100 mL receiving flask. The apparatus was placed under vacuum for one hour, then backfilled with nitrogen. The distillation head was removed, and tin (II) ethyl hexanoate (50 µL) was added to the reaction flask by syringe under nitrogen flow. The apparatus was reassembled, then purged under vacuum and backfilled with nitrogen 3 times. The reaction flask was immersed in an oil bath that was warmed to 180° C. with constant flow of nitrogen into the 2-neck flask through the distillation adapter and out of the vacuum adapter to room atmosphere. The reaction was stirred for three hours and then cooled to room temperature under nitrogen flow, affording the product, a UV-absorbing polyglycerol, as a yellow solid. $^1$H NMR (400 MHz, CDCl$_3$) δ ppm 11.81 (br. s., 2 H), 8.15 (br. s., 2 H), 7.75-8.02 (br. s, 4 H), 7.34-7.58 (br. s, 4 H), 7.21 (br. s., 2 H), 4.93-5.32 (br, 1 H), 3.17-4.50 (br. m, 38 H), 2.86-3.11 (br. m, 4H), 2.54-2.84 (br. m, 4 H), 2.31 (br. s., 2 H), 1.61 (br. s., 2 H), 1.50 (br. s., 18 H), 1.26 (br. s., 28 H), 0.89 (t, J=6.3 Hz, 3 H). GPC (THF): $M_w$ 1700; $M_n$ 950.

Example 10

Synthesis of benzotriazole acid methyl ester

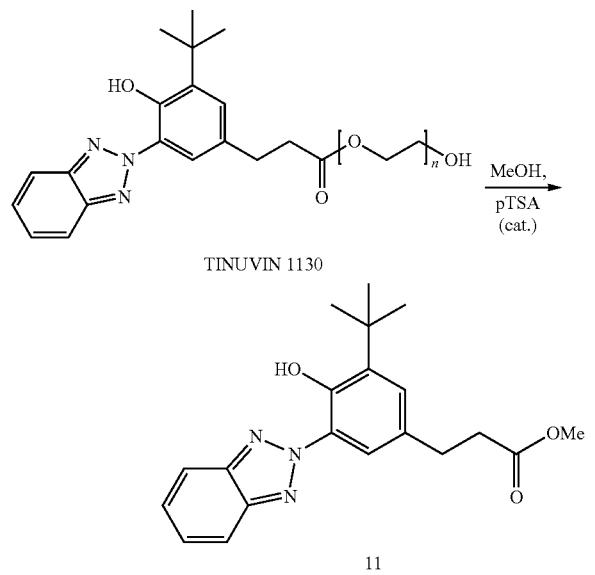

FORMULA XVI. SYNTHESIS OF METHYL ESTER 11

The synthesis of benzotriazole methyl ester 11 intended for transesterification with a polymer with hydroxyl functional groups is illustrated in FORMULA XVI. Beta-[3-(2-H-benzotriazole-2-yl)-4-hydroxy-5-tert-butylphenyl]-propionic acid-poly(ethylene glycol) 300-ester (50.1 g; a UV absorbing product sold under the trade name TINUVIN 1130 by BASF Corporation, Wyandotte, Mich.) was added to a 2-neck 1 liter round bottom flask containing a magnetic stir bar. Methanol (500 mL) was added to the flask. The flask was immersed in an oil bath; the solution was stirred. p-TSA.H$_2$O (0.63 g) was added to the solution. The 2-neck flask was fitted with a reflux condenser and rubber septum; the stirred reaction mixture was brought to reflux by warming the oil bath; reflux was maintained for 17 hours. The flask was then removed from the oil bath and allowed to cool to room temperature, whereupon the product precipitated as a white solid. The precipitate was isolated by vacuum filtration, and then recrystallized from methanol; the solids were isolated by vacuum filtration and dried under vacuum at 80° C. affording the benzotriazole methyl ester 11 (18.27 g) as a white solid. $^1$H NMR (400 MHz, CDCl$_3$) δ ppm 11.81 (s, 1 H), 8.16 (d, J=2.1 Hz, 1 H), 7.90-7.98 (m, 2 H), 7.45-7.53 (m, 2 H), 7.22 (d, J=2.2 Hz, 1 H), 3.71 (s, 3 H), 3.01 (t, J=7.8 Hz, 2 H), 2.71 (t, J=7.8 Hz, 2 H), 1.51 (s, 9 H).

Example 11

Transesterification of benzotriazole methyl ester with polyglycerol polymer

FORMULA XVII.
TRANSESTERIFICATION OF WITH POLYGLYCEROL

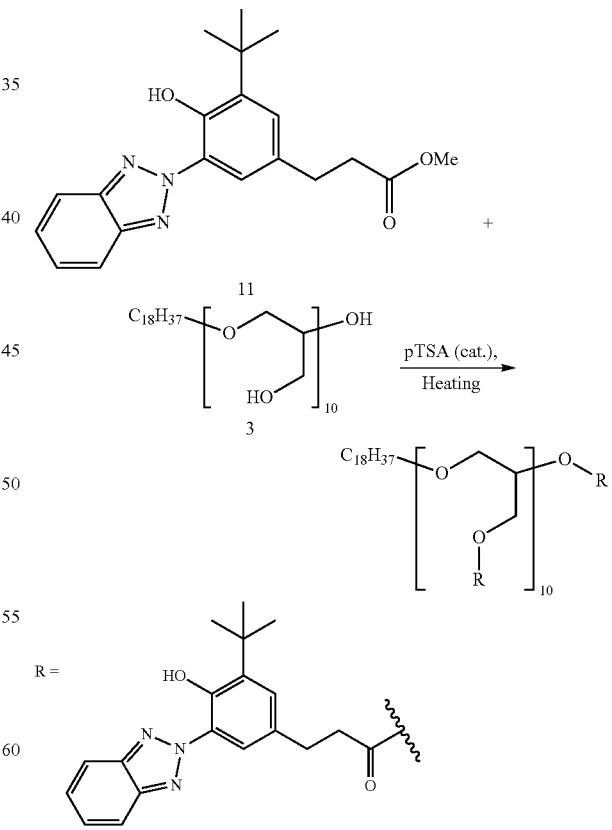

The transesterification of benzotriazole methyl ester 11 with polyglycerol 3 is illustrated in FORMULA XVII. A solution of polyglycerol 3 solution in MeOH was concentrated by rotary evaporation; residual solvent was removed overnight under vacuum at 75° C. Polyglycerol 3 (1.36 g, 14.9 hydroxyl milliequivalents) was added to a 100 mL 2-neck round bottom flask containing a magnetic stir bar. Benzotriazole methyl ester 11 (4.24 g, 12 mmol) and pTSA.H$_2$O (7.1 mg) was added to the flask. The flask was fitted with a nitrogen inlet adapter and distillation adapter with 100 mL receiving flask. The reaction flask was immersed in an oil bath, and the oil bath was warmed to 175° C. Within 20 minutes, all of the reactants had melted. The reaction mixture was stirred vigorously under a stream of nitrogen overnight. The following morning, the flask was placed under vacuum; residual UV-chromophore sublimed and collected in the distillation adapter. Heating under vacuum was continued overnight. The reaction mixture was then cooled to room temperature; the UV-absorbing polyglycerol product was obtained as a yellow, glassy solid. $^1$H NMR (400 MHz, CDCl$_3$) δ ppm 11.71 (br. s., 8 H), 8.05 (br. s., 8 H), 7.81 (br. s., 16 H), 7.36 (br. s., 16H), 7.14 (br. s., 8 H), 5.06-5.32 (br. s., 1 H), 3.86-4.57 (m, 16 H), 3.15-3.82 (m, 30 H), 2.92 (br. s., 16 H), 2.68 (br. s., 16 H), 1.45 (br. s., 76 H), 1.24 (br. s., 28 H), 0.88 (t, J=6.6 Hz, 3 H).

It can be seen from Examples 1-11 that analytical characterization of the resulting UV-absorbing polyethers was consistent with the expected structures. HPLC analysis of the polymers described in the examples provided evidence that the polymerization methods described resulted in low concentrations of residual UV absorbing monomer.

Example 12

Summary of SPF Results

Sun protection factor (SPF) measurements for UV absorbing polymers were performed using the following in vitro sun protection test method. Polymer samples were measured into 8 mL glass vials. Mixed C$_{12}$ to C$_{15}$ alkyl benzoates (a cosmetic oil solvent sold under the trade name FINSOLV TN by Innospec, Newark, N.J.) was added to the vial to achieve the desired weight percent solution of polymer. A magnetic stir bar was added to the vial, which was then sealed with a Teflon lined screw cap. The polymer/oil solution was stirred in a 100° C. aluminum reaction block until homogeneous. Once cooled, 32 mg of polymer solution was applied to a poly(methyl methacrylate) (PMMA) plate (a test substrate sold under the trade name HELIOPLATE HD6 by Helioscience, Marseille, France). The solution was spread evenly over the plate using one finger using a latex cot until the weight of sample on the plate had decreased to 26 mg. The baseline transmission was measured using an HD6 plate as received from the manufacturer. Absorbance was measured using a calibrated Labsphere UV-1000S UV transmission analyzer (Labsphere, North Sutton, N.H., USA). The absorbance measures were used to calculate SPF indices. SPF was calculated using methods known in the art. The equation used for calculation of SPF is described by Equation 1.

$$SPF_{in\ vitro} = [\int E(\lambda)I(\lambda)d\lambda]/[\int E(\lambda)I(\lambda)10^{-A_0(\lambda)}(d\lambda)] \quad (1)$$

where:
E(λ)=Erythema action spectrum
I(λ)=spectral irradiance received from the UV source
A$_0$(λ)=mean monochromatic absorbance of the test product layer before UV exposure
dλ=Wavelength step (1 nm)
and the integrations are each performed over the wavelength range from 290 nm to 400 nm.

Results of in vitro SPF testing of the polymers are reported in Examples 4, 7, and 9 as [wt. % in FINSOLV TN, mean SPF value] and are also shown in Table 1.

TABLE 1

| Polymer of example # | Polymer concentrations (wt %) | SPF | STDEV |
|---|---|---|---|
| 7 | 40 | 25 | |
| 4 | 40 | 32 | 11 |
| 9 | 40 | 31 | 8 |

It can be seen that the UV-absorbing polyethers described were soluble in oils commonly used in topical cosmetic applications. Furthermore, it was demonstrated that solutions of polymers in these oils showed suitable SPF values using in vitro SPF test methods.

The invention claimed is:

1. A composition comprising a cosmetic oil solvent and a polymer composition comprising a linear ultraviolet radiation absorbing polyether that comprises a covalently bound UV-chromophore and a backbone comprising glyceryl repeat units.

2. The composition of claim 1, wherein the cosmetic oil solvent comprises alkyl benzoates.

3. The composition of claim 1 having an SPF of about 25 or greater.

4. The composition of claim 1, wherein the linear ultraviolet radiation absorbing polyether comprises a repeat unit of the formula:

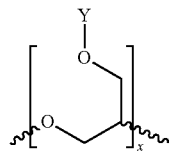

where Y is the covalently bound UV-chromophore.

5. The composition of claim 1, wherein the polymer composition comprises about 50 or more of said linear ultraviolet radiation absorbing polyether.

6. The composition of claim 1, wherein the UV-chromophore is a benzotriazole.

7. The composition of claim 1, wherein the UV-chromophore absorbs both UVA and UVB radiation.

8. The composition of claim 1, wherein the polymer composition has a weight average molecular weight of about 500 to about 50,000.

9. A linear ultraviolet radiation absorbing polyether prepared by the process of transesterification of a linear polyglycerol containing side chain hydroxyl groups and a UV-chromophore ester.

10. The polyether of claim 9, wherein transesterification is performed using an acid catalyst.

11. The polyether of claim 9, wherein the UV chromophore is a benzotriazole.

12. The polyether of claim 9, wherein the UV-chromophore absorbs both UVA and UVB radiation.

13. The polyether of claim 9 having a weight average molecular weight of about 500 to about 50,000.

* * * * *